United States Patent
Ueno

(10) Patent No.: US 9,460,245 B2
(45) Date of Patent: Oct. 4, 2016

(54) METHOD FOR SIMULATING POLYMER MATERIAL

(71) Applicant: Sumitomo Rubber Industries, Ltd., Kobe-shi, Hyogo (JP)

(72) Inventor: Shinichi Ueno, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 669 days.

(21) Appl. No.: 13/901,795

(22) Filed: May 24, 2013

(65) Prior Publication Data

US 2013/0346045 A1 Dec. 26, 2013

(30) Foreign Application Priority Data

Jun. 21, 2012 (JP) .................................. 2012-140049
Oct. 5, 2012 (JP) .................................. 2012-223410

(51) Int. Cl.
| | | |
|---|---|---|
| *G06G 7/48* | (2006.01) | |
| *G06F 17/50* | (2006.01) | |
| *G06F 19/00* | (2011.01) | |

(52) U.S. Cl.
CPC ......... *G06F 17/5009* (2013.01); *G06F 19/701* (2013.01); *G06F 19/704* (2013.01)

(58) Field of Classification Search
CPC . G06F 17/5009; G06F 19/701; G06F 19/704
See application file for complete search history.

(56) References Cited

FOREIGN PATENT DOCUMENTS

JP 2006-064658 A 3/2006

OTHER PUBLICATIONS

Yagyu, Hiromasa, and Takayuki Utsumi. "Coarse-grained molecular dynamics simulation of nanofilled crosslinked rubber." Computational Materials Science 46.2 (2009): 286-292.*

Vladkov, Mihail. Modeling interfacial effects on transport properties: mechanical properties of polymers, thermal properties of nanofluids. Diss. Université Claude Bernard-Lyon I, 2007.*

Knauert, Scott T., Jack F. Douglas, and Francis W. Starr. "The effect of nanoparticle shape on polymer-nanocomposite rheology and tensile strength." Journal of Polymer Science Part B: Polymer Physics 45.14 (2007): 1882-1897.*

Blomqvist, Janne. "Modeling of polymer-metal hybrid materials." (2012).*

Yasuhiro Senda, Miyuki Fujio, Shuji Shimamura, Janne Blomqvist, Risto M Nieminen, Fast convergence to equilibrium for long-chain polymer melts using a MD/continuum hybrid method, May 30, 2012, 13 pages.*

(Continued)

*Primary Examiner* — Aniss Chad
(74) *Attorney, Agent, or Firm* — Birch, Stewart, Kolasch & Birch, LLP

(57) ABSTRACT

A computer-implemented method for simulating a polymer material comprising a polymer, a filler and a modifying agent for increasing the affinity of the polymer to the filler is disclosed. In order to make a relaxation calculation of filler models and modified polymer models in a short period of time, a pair of filler models are defined by a pair of parallelly-opposed wall surfaces of a virtual space in which the modified polymer models are disposed, and a molecular dynamics calculation is performed.

2 Claims, 12 Drawing Sheets

(56) References Cited

OTHER PUBLICATIONS

Cameron F. Abrams, Inhomogeneous Coarse-Graining of Polymers and Polymer/Metal Interfaces, Computational Soft Matter: From Synthetic Polymers to Proteins, Lecture Notes, Norbert Attig, Kurt Binder, Helmut Grubm uller, Kurt Kremer (Eds.), John von Neumann Institute for Computing, Julich, NIC Series, vol. 23, ISBN 3-00-012641-4, pp. 275-288, 2004.*

Kurt Kremer and Gary S. Grest, Dynamics of entangled linear polymer melts: A molecular-dynamics simulation, The Journal of Chemical Physics 92, pp. 5057-5086 (1990).*

* cited by examiner

METHOD FOR SIMULATING POLYMER MATERIAL

BACKGROUND OF THE INVENTION

The present invention relates to a computer-implemented method for simulating a polymer material comprising a polymer, a filler and a modifying agent for increasing the affinity of the polymer to the filler, more particularly to a combination of a modified polymer model and a filler model which is specifically defined by a flat surface fixed to a small virtual space in which the modified polymer models are disposed.

In general, a rubber compound used in a pneumatic tire contains reinforcing filler such as carbon black and silica. For example, if a silica-rich compound is used as a tread rubber of a pneumatic tire, an internal energy loss of the tread rubber is decreased and the tire performance, e.g. rolling resistance may be improved. Such silica-rich compound contains a modifying agent (coupling agent such as Silane) to improve the affinity of the base rubber or elastomer to the silica filler (namely, the bond therebetween). If the affinity is low, the strength of the rubber compound is decreased with the increase in the content of the filler.

In recent years, on the other hand, in order to develop a rubber compound, the use of a computer simulation is proposed.

Japanese Patent Application Publication No. 2006-064658 discloses a computer-implemented method for evaluating a rubber material containing rubber and carbon black, and teaches to use a carbon model defined according to the molecular structure of the carbon black namely a graphite structure containing carbon atoms and a rubber model defined according to the molecular structure of the base rubber.

If such carbon models and rubber models are arranged dispersively, freely-movably in a virtual space, and a relaxation calculation is made based on molecular dynamics, it takes much time to complete the relaxation calculation.

SUMMARY OF THE INVENTION

It is therefore an object of the present invention to provide a method for simulating a polymer material, in which a relaxation calculation with respect to filler models and rubber polymer models can be completed in a short period of time, and therefore, the dispersion of the rubber polymer modified by a modifying (coupling) agent can be simulated in a short period of time.

According to the present invention, a computer-implemented method for simulating a polymer material comprising a polymer, a filler, and a modifying agent for increasing the affinity of the polymer to the filler, comprises:
a process in which a virtual space is defined so that the virtual space has a pair of parallelly-opposed wall surfaces;
a process in which a plurality of modified polymer models are defined in the virtual space,
wherein each of the modified polymer models includes
a polymer model of the polymer, comprising at least one particle, and
a modifying agent model of the modifying agent, comprising at least one particle representing a modifying group of the modifying agent;
a process in which,
between the particles of the polymer models,
between the particles of the modifying agent models and
between the particles of the polymer models and the particles of the modifying agent models,
a repulsive potential which exerts a repulsive force between the particles concerned when the distance therebetween becomes less than the predetermined threshold, is defined;
a process in which a pair of filler models are defined by the parallelly-opposed wall surfaces of the virtual space;
a process in which, between the filler models and the particles of the polymer models and
between the filler models and the particles of the modifying agent models,
a potential which exerts an attractive force between the filler model and the particle concerned when the distance therebetween becomes less than a predetermined threshold, is defined, wherein
the threshold for the potential between the filler model and the particle of the modifying agent model is larger than the threshold for the potential between the filler model and the particle of the polymer model, and
the intensity of the potential between the filler model and the particle of the modifying agent model is larger than the intensity of the potential between the filler model and the particle of the polymer model; and
a simulation process in which a relaxation of the modified polymer models in the virtual space and the filler models is performed by making a molecular dynamics calculation.

Preferably, the simulation process includes a first calculation process and a second calculation process performed thereafter, wherein
the first calculation process is such that, with respect to every combinations of the particles of the modified polymer models, the repulsive potential is defined so that the resultant repulsive force is always zero, and under such condition, a molecular dynamics calculation is performed, and
the second calculation process is such that a molecular dynamics calculation is performed normally without mandatorily setting zero to the repulsive force resulted from the repulsive potential.

In each of the modified polymer models, the polymer model comprises a plurality of the particles, and preferably, between the particles of the polymer model, and
between the particle of the polymer model and the particle of the modifying agent model,
a joining chain is defined by a coupling potential, wherein the coupling potential is defined between the particles concerned so that, when the distance therebetween becomes increased over a distance which is determined by the intensity of the repulsive potential and the intensity of the coupling potential, the coupling potential dominantly exerts an attractive force whose magnitude is larger than the magnitude of the repulsive force resulting from the repulsive potential defined between the particles concerned.

Therefore, the filler models are fixed to the virtual space. Under such condition, to be calculated is the dispersion or motions of the modified polymer models. Accordingly, the relaxation calculation can be completed in a short period of time.

DESCRIPTION OF THE PREFERRED EMBODIMENTS

Embodiments of the present invention will now be described in detail in conjunction with accompanying drawings.

The simulation method according to the present invention is to simulate a polymer material or mixture comprising a polymer, a filler and a modifying agent to increase the affinity of the polymer to the filler and thus, can be used to evaluate the effect of the modifying agent and to estimate the characteristics of the cured polymer material.

Here, the filler may be any kind of filler including carbon black, silica, alumina and the like.
The polymer may be any kind of polymer including rubber, elastomer, resin and the like.
The modifying agent may be any kind of modifying agent having a functional group which is an atom group including a hydroxyl group or carbonyl group.

Figure 1:
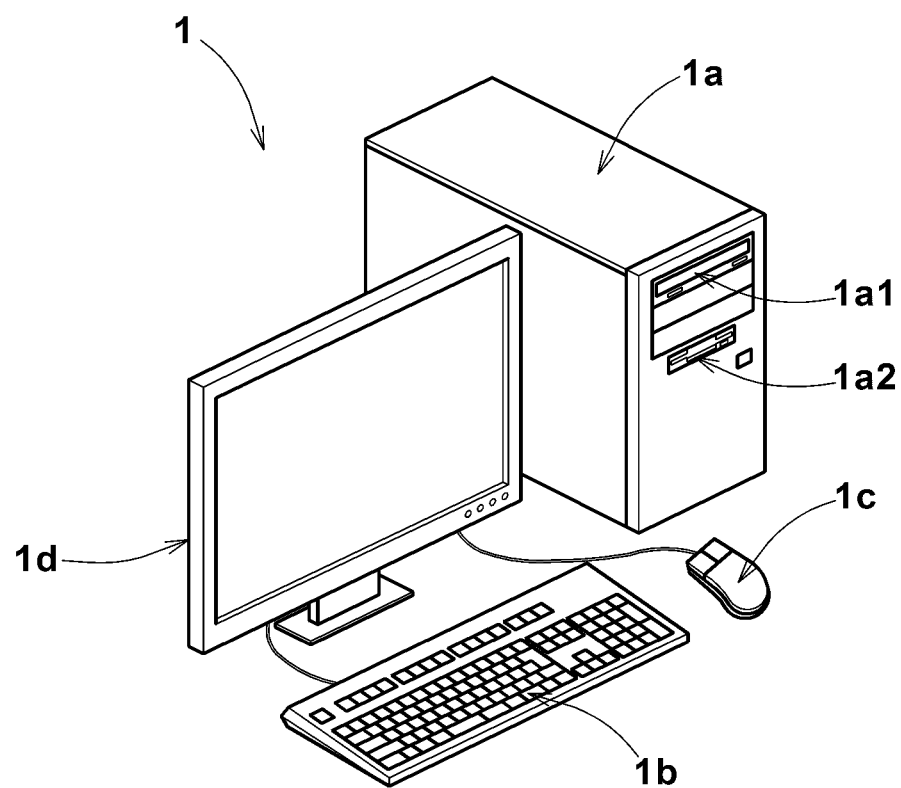
FIG. 1 is a perspective view of a computer system for implementing a simulation method as an embodiment of the present invention.

As shown in FIG. 1 for example, the computer system 1 implementing the simulation method comprises a main body 1a, a keyboard 1b, a mouse 1c and a display 1d. The main body 1a comprises an arithmetic processing unit (CPU), memory, storage devices such as magnetic disk, disk drives 1a1 and 1a2 and the like. In the storage device, programs/software for carrying out the simulating method are stored.

Figure 2:
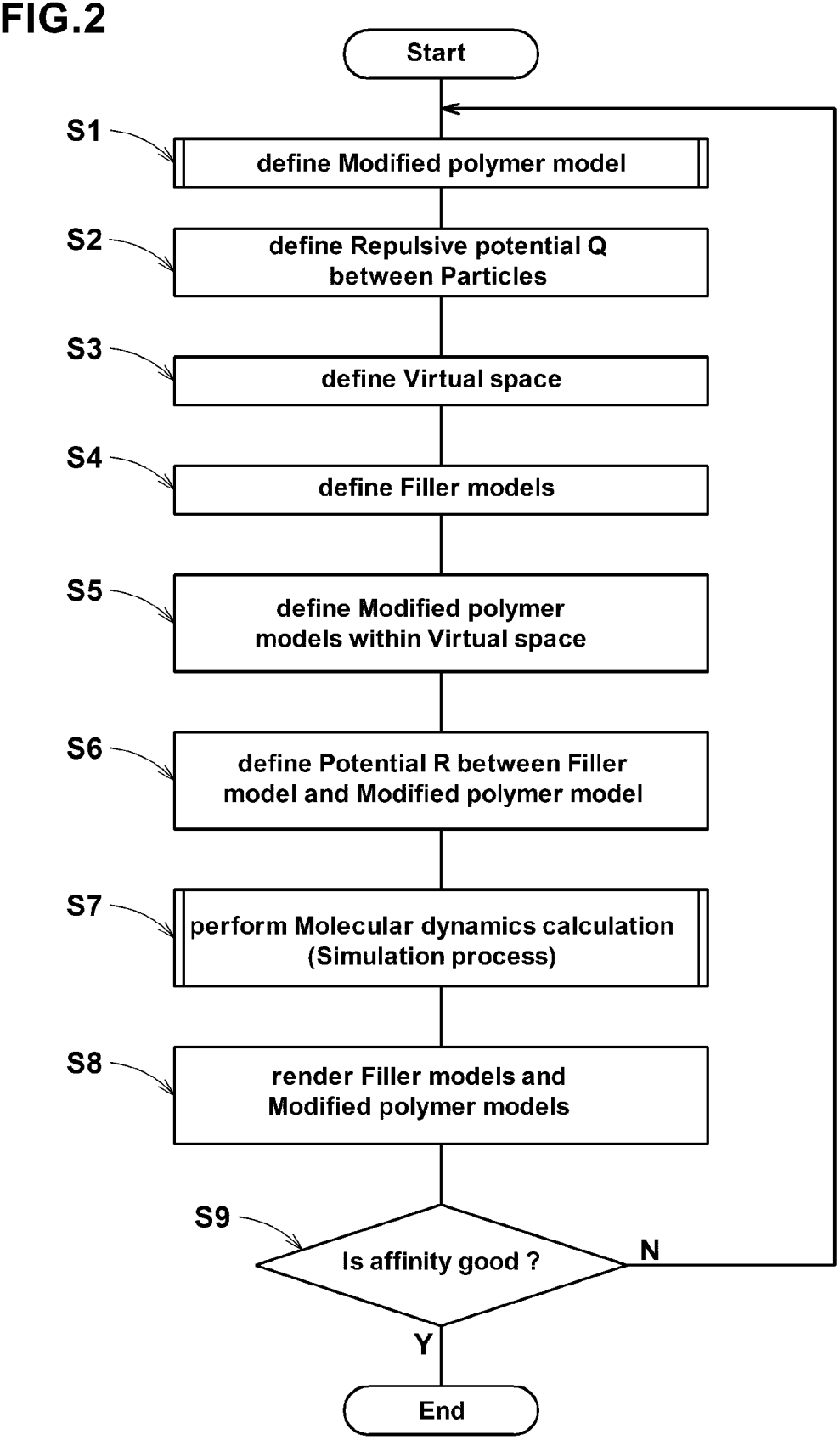
FIG. 2 is a flow chart of the simulation method.

FIG. 2 shows a flowchart of the simulation method as an embodiment of the present invention.

This flowchart is just for illustrative purposes. It is not always necessary to perform these processes in this order.

Process S1

Figure 3:
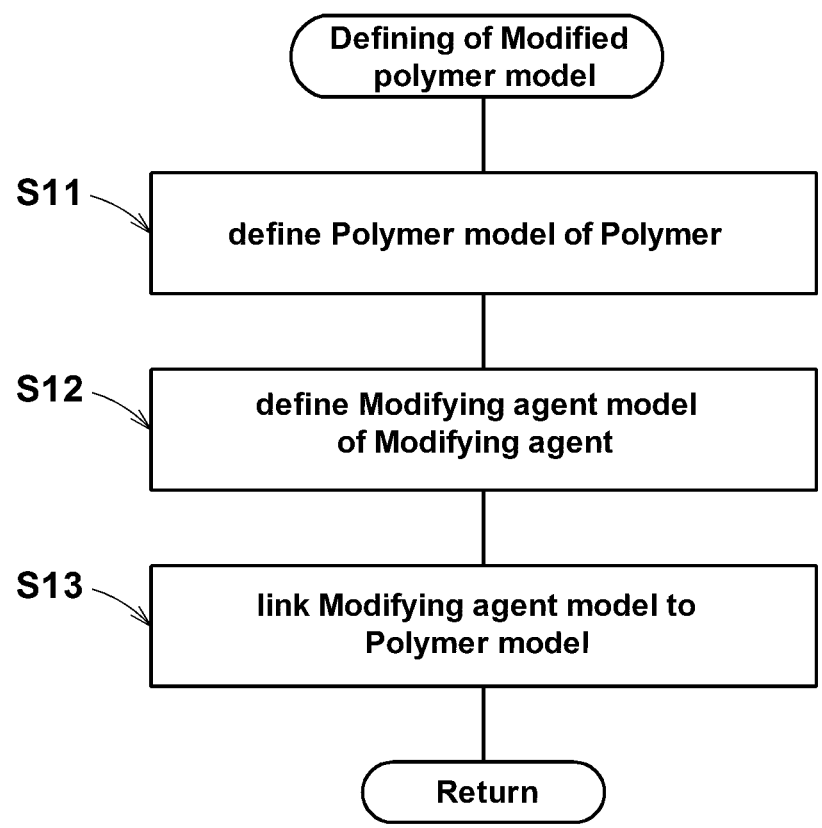
FIG. 3 is a flow chart of the process for defining the modified polymer model.

In the process S1, a modified polymer model 2 made up of a polymer model 3 and a modifying agent model 7 is defined, FIG. 3 shows a flowchart of this process S1.

Process S11

In the process S11, a polymer model 3 of the polymer is defined.

Figure 4:
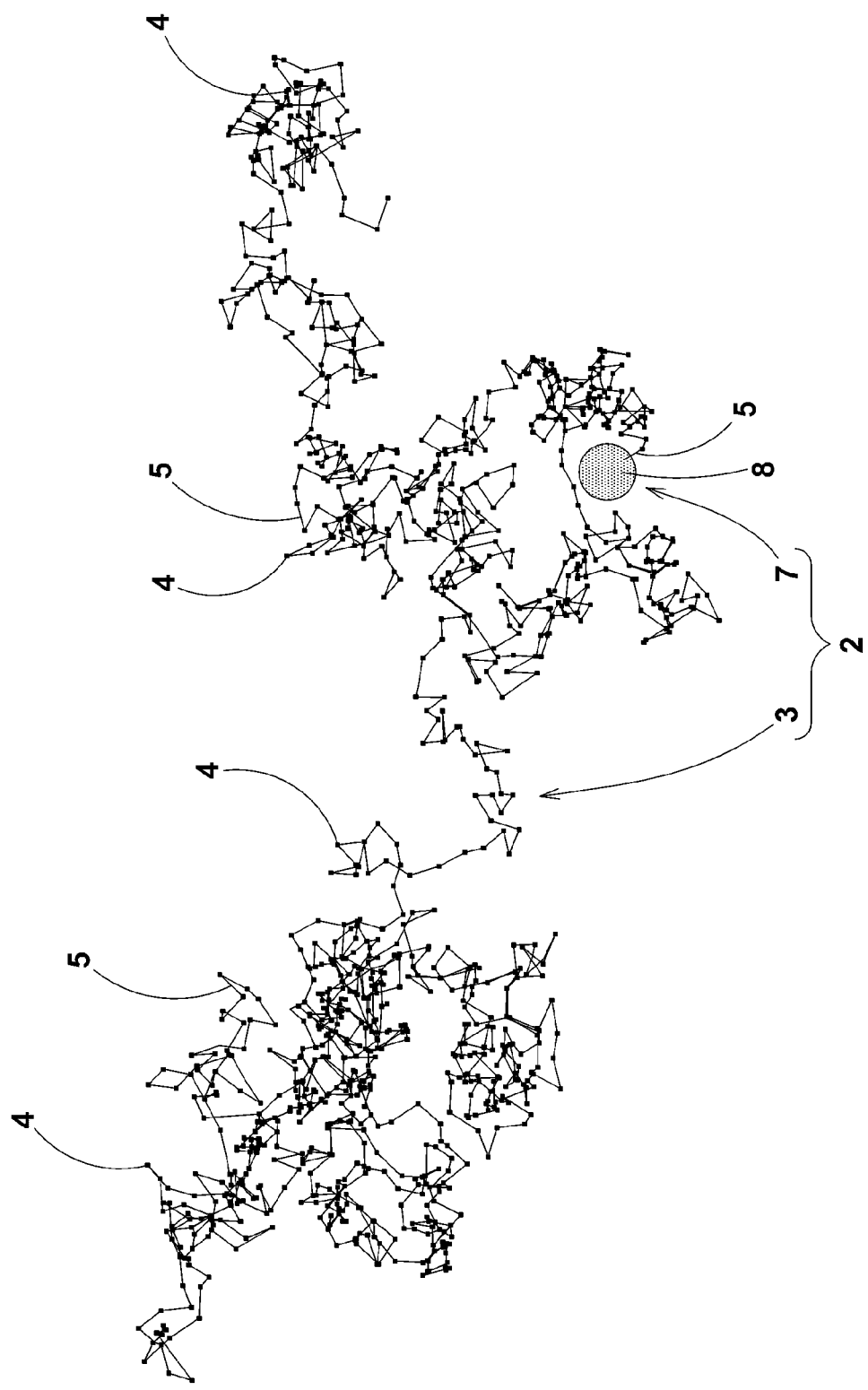
FIG. 4 shows an example of the modified polymer model.

As shown in FIG. 4, the polymer model 3 comprises at least one, in this example, a plurality of particles 4 defined according to a coarse-grained molecular dynamic method so that each particle 4 represents a plurality of monomers.

The polymer model 3 is, of course, a set of numerical data (inclusive of data on the mass, volume, diameter and initial stage coordinates of each particle 4) to be used in a molecular dynamics calculation, and the numerical data are stored in the computer 1.

Figure 5:
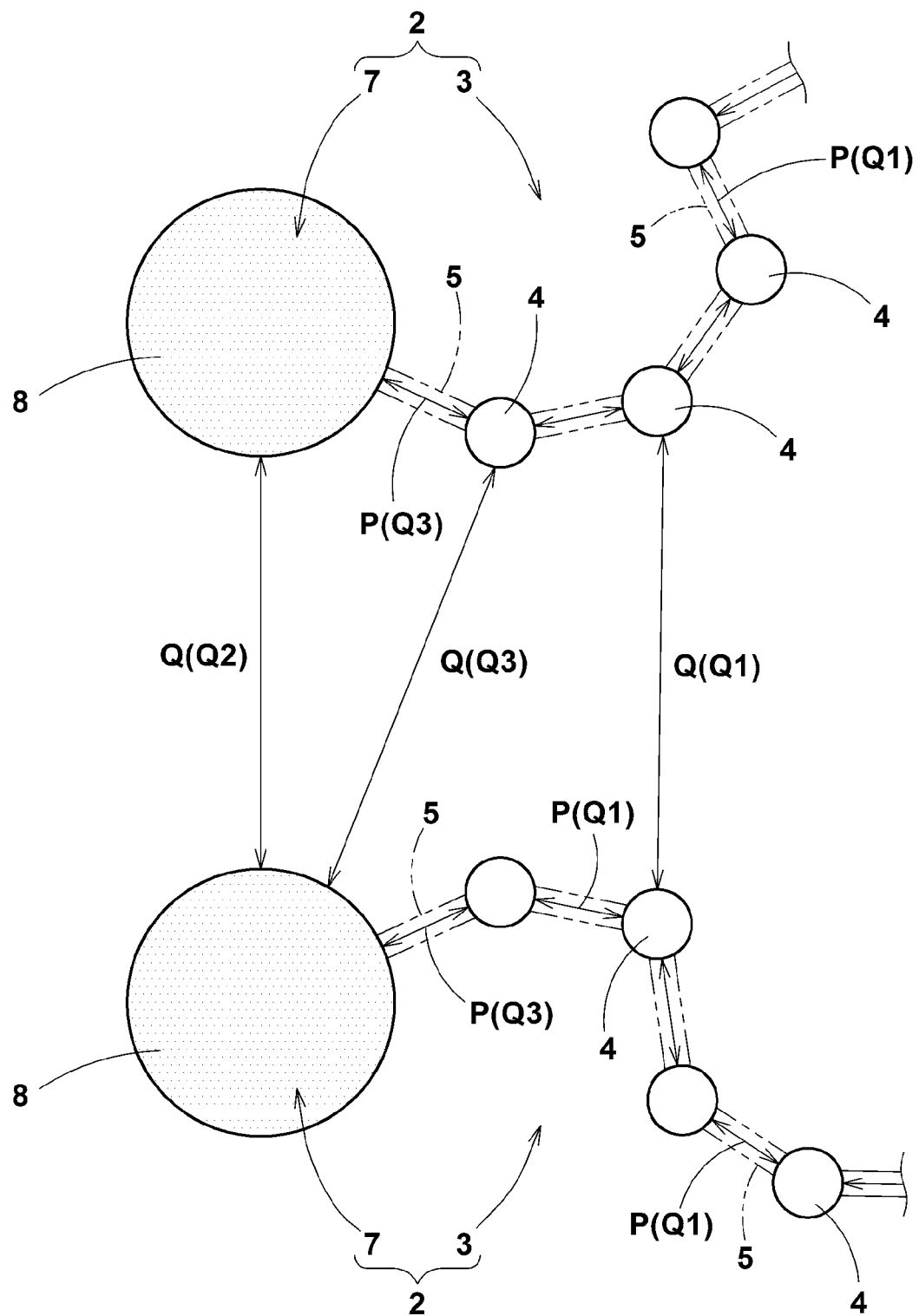
FIG. 5 shows two adjacent modified polymer models.

In this example, one polymer model 3 includes a large number of the particles 4, and as shown in FIG. 5, between the particles 4, a joining chain 5 is defined so that the distance therebetween is variable to a limited extent.
The polymer model 3 represents a three-dimensional straight-chain structure of the polymer.

The joining chain 5 is defined by a coupling potential P given by the following equation (1).

$$P = \begin{cases} -0.5kR_0^2 \ln\left[1 - \left(\frac{r_{ij}}{R_0}\right)^2\right] & \text{if } r_{ij} < R_0 \\ \infty & \text{if } r_{ij} \geq R_0 \end{cases} \quad (1)$$

wherein
k: a coefficient for the intensity of the coupling potential P between the particles 4 concerned,
$r_{ij}$: the distance between the centers of the particles 4 concerned, and
$R_0$: a predetermined allowable maximum distance between the centers of the particles 4 concerned.

In the equation (1), therefore, when the distance $r_{ij}$ is less than the allowable maximum distance $R_0$, the coupling potential P restricts the relative motion of the particles 4 according to the distance $r_{ij}$ between the particles 4 so that the distance $r_{ij}$ may be restored to the original.

If however, the value of the distance $r_{ij}$ becomes increased over the allowable maximum distance $R_0$, then infinity is set to the coupling potential P so that the distance $r_{ij}$ does not increase over the allowable maximum distance $R_0$. Thus, the joining chain 5 is defined to have an elongation limit.

As to the coefficient k for the intensity of the coupling potential P and the allowable maximum distance $R_0$, any suitable values may be set thereto. In this embodiment, "30" is set to the coefficient k, and
"1.5" is set to the allowable maximum distance $R_0$ according to Non-patent document ("Dynamics of entangled linear polymer melts; A molecular-dynamics simulation" Journal of Chemical Physics, volume 92, Issue 8, 15 Apr. 1990)

Process S12

In the process S12, a modifying agent model 7 of the modifying agent is defined.

The modifying agent model 7 comprises at least one particle 8, in this example as shown in FIG. 4 and FIG. 5 only one particle 8, representing a modifying group or a functional group of the modifying agent.

Similarly, the modifying agent model 7 is a set of numerical data (inclusive of data on the mass, volume, diameter and initial stage coordinates of particle 8) to be used in the molecular dynamics calculation. The numerical data are stored in the computer 1.

Process S13

In the process S13, the modifying agent model 7 is linked to the polymer model 3, and a modified polymer model 2 which is made up of the polymer model 3 and the modifying agent model 7 is defined, wherein,
in order to link between the particle 8 of the modifying agent model 7 and one of the particles 4 of the polymer model 3, a joining chain 5 as described above is defined by the above-mentioned coupling potential P given by the equation (1).

Process S2

In the process S2, between the particles 4 and 4 of the polymer model 3, between the particles 8 and 8 of the modifying agent model 7 (if plural particles 8 exist), and between the particle 4 and particle 8, a repulsive potential Q given by the following equation (2), is defined.

$$Q = \begin{cases} 4\varepsilon\left[\left(\dfrac{\sigma}{r_{ij}}\right)^{12} - \left(\dfrac{\sigma}{r_{ij}}\right)^{6} + \dfrac{1}{4}\right] & \text{if } r_{ij} < 2^{\frac{1}{6}}\sigma \\ 0 & \text{if } r_{ij} \geq 2^{\frac{1}{6}}\sigma \end{cases} \quad (2)$$

wherein
$\varepsilon$: a coefficient for the intensity of the repulsive potential Q between the particles concerned,
$r_{ij}$: the distance between the centers of the particles concerned,
$\sigma$: a coefficient for adjusting the threshold of the distance $r_{ij}$.
These coefficients and variable correspond to the parameters of Lennard-Jones potential.

In the equation (2), when the distance $r_{ij}$ is less than the predetermined threshold $2^{1/6}\sigma$, the repulsive potential Q is increased with the decrease in the distance $r_{ij}$, and the repulsive potential Q becomes equal to the above-mentioned coupling potential P. Thereby,
the distance between the particles 4 and 4 between which the joining chain 5 is defined, and
the distance between the particle 4 and particle 8 between which the joining chain 5 is defined,
are stably-maintained, and the modified polymer model 2 can maintain its three-dimensional straight-chain structure.

If however, the value of the distance $r_{ij}$ becomes less than the threshold $2^{1/6}\sigma$, then zero is set to the repulsive potential Q so that the repulsive force becomes zero.

The repulsive potential Q is also defined between the modified polymer models 2 and 2. In the example shown in FIG. 5, the following repulsive potentials Q1 to Q3 are defined.
Q1: between particle 4 and particle 4 in each modified polymer model 2,
Q1: between particle 4 in a modified polymer model 2 and particle 4 in another modified polymer model 2
Q2: between particle 8 in a modified polymer model 2 and particle 8 in another modified polymer model 2
Q3: between particle 4 and particle 8 in each modified polymer model 2,
Q3: between particle 4 in a modified polymer model 2 and particle 8 in another modified polymer model 2

Any suitable values may be set to the coefficient $\varepsilon$ of each of the repulsive potentials Q1 to Q3. In this embodiment, "1.0" is set to each, according to the above-mentioned Non-patent document so that the repulsive potentials Q1 to Q3 may have an identical intensity.

Process S3

In the process S3, there is defined a virtual space 6 having a predetermined volume and a pair of parallelly-opposed wall surfaces 11 and 11 between which the modified polymer model 2 is disposed.

Process S4

In the process S4, a pair of filler models 12 and 12 are respectively defined by a pair of the above-mentioned parallelly-opposed wall surfaces 11 and 11.
Namely, according to the present invention, each filler model 12 is defined by a flat face instead of a particle (or spherical surface).

Figure 6:
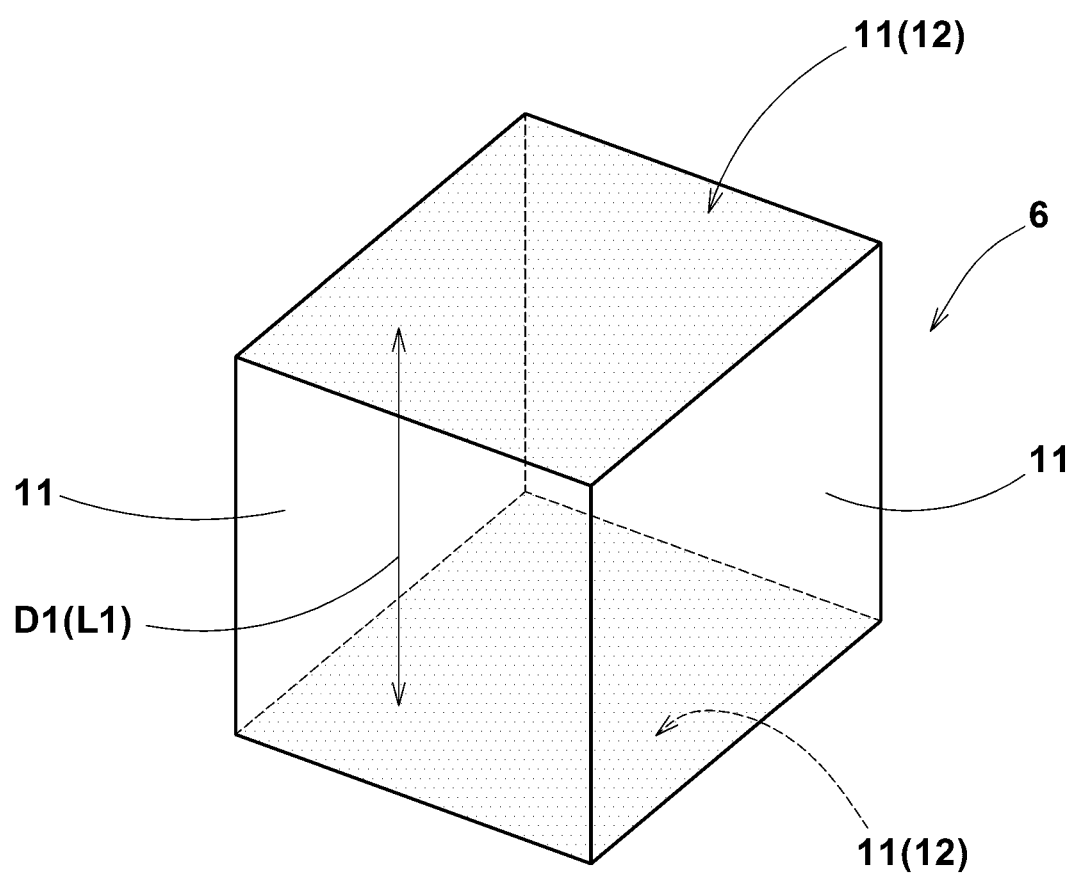
FIG. 6 is a perspective view of an example of the virtual space.

In the example shown in FIG. 6, the wall surfaces 11 and 11 which are parallelly-opposed in the up-and-down direction are used to define the filler models 12 and 12, respectively. The paired filler models 12 are accordingly immovable with respect to the virtual space 6.

Process S5

Figure 8:
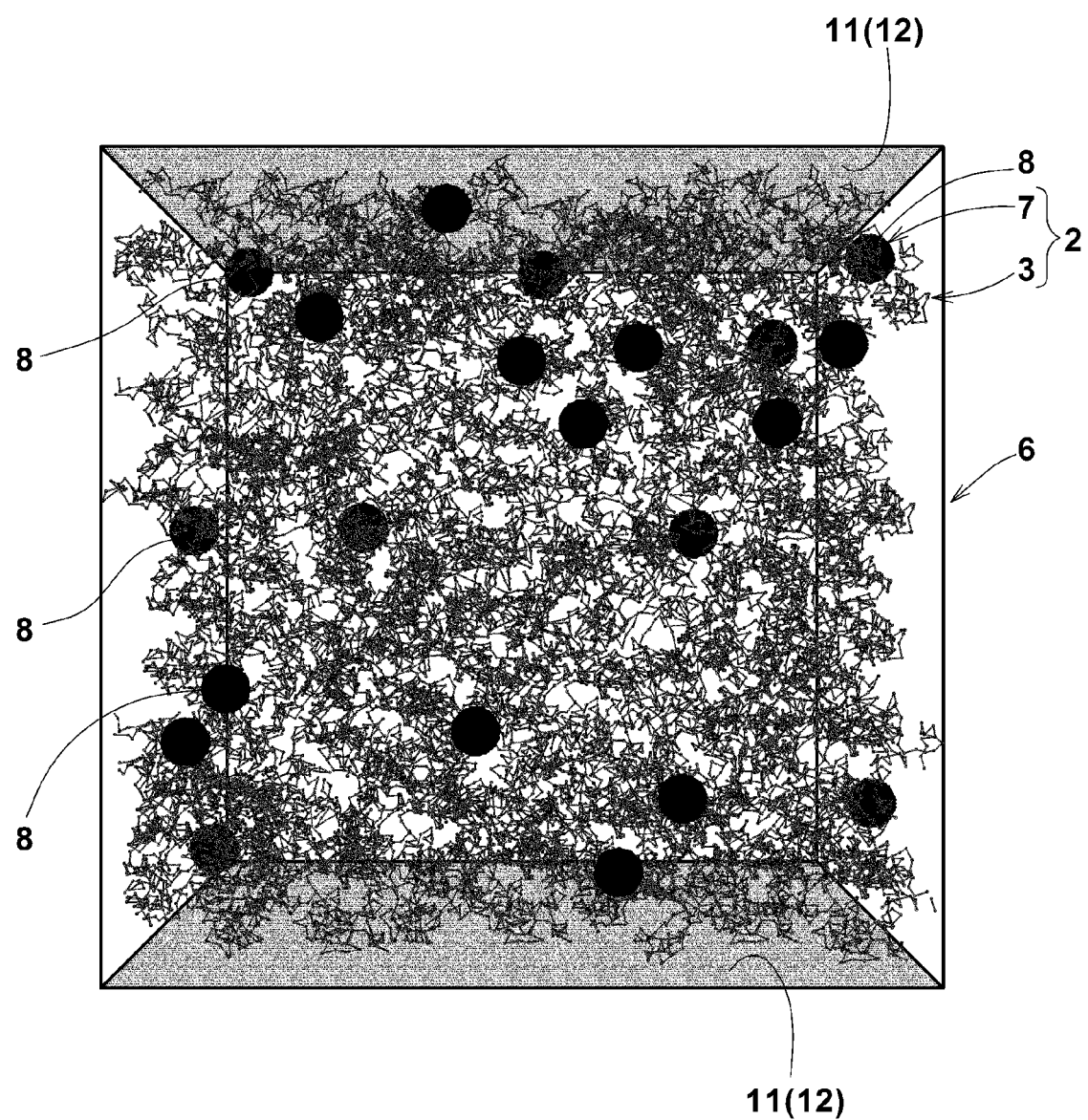
FIG. 8 shows an initial state of the modified polymer models disposed in the virtual space.

In the process S5, as shown in FIG. 8, a plurality of the modified polymer models 2 are arranged or defined within the virtual space 6, namely between the paired filler models 12 and 12. In the example shown in FIG. 8, each black circle represents one particle 8. Initially, the modified polymer models 2 are arranged randomly. But, it is also possible to arrange periodically.

As to the size of the virtual space, the distance D1 (length L1 of a side) between the paired parallelly-opposed wall surfaces 11 measured perpendicularly thereto is preferably not less than 2 times, preferably not less than 4 times the radius of inertia of the modified polymer model 2.
Thereby, in the after-mentioned molecular dynamics calculation, it becomes possible to stably calculate the rotational motion of the modified polymer model 2 in the virtual space 6.

For example, when the radius of inertia is in a range of from $5\sigma$ to $10\sigma$, the distance D1 is preferably set in a range of from $20\sigma$ to $40\sigma$.

Process S6

In the process S6, between the filler model 12 and the modified polymer model 2, there is defined a potential R which can exert an attractive force or a repulsive force therebetween according to their distance. In the example shown in FIG. 7, between the filler model 12 and the particle 4 (simulating a non-modified group), and
between the filler model 12 and the particle 8 (simulating a modified group),
the potential R given by the following equation (3) is defined.

$$R = \begin{cases} 4\pi\rho_{wall}\varepsilon_{wall}\left[\dfrac{1}{5}\left(\dfrac{\sigma_{wall}}{r}\right)^{10} - \dfrac{1}{2}\left(\dfrac{\sigma_{wall}}{r}\right)^{4}\right] & \text{if } r < r_c \\ 0 & \text{if } r \geq r_c \end{cases} \quad (3)$$

wherein
r: the distance between the filler model and the particle 4 or 8 concerned,
$r_c$: a threshold of the distance,
$\rho_{wall}$: a coefficient relating to the areal density of the potential R
$\varepsilon_{wall}$: a coefficient relating to the intensity of the potential R
$\sigma_{wall}$: a coefficient relating to the distance from the filler model (wall surface 11).

The equation (3) is obtained by integrating the equation (2) over the wall surface 11 (the filler model 12).
In the equation (3), if the distance r is less than $2^{1/6}\sigma_{wall}$, the potential R exerts a repulsive force.
If the distance r is more than $2^{1/6}\sigma_{wall}$, the potential R exerts an attractive force.

Figure 7:
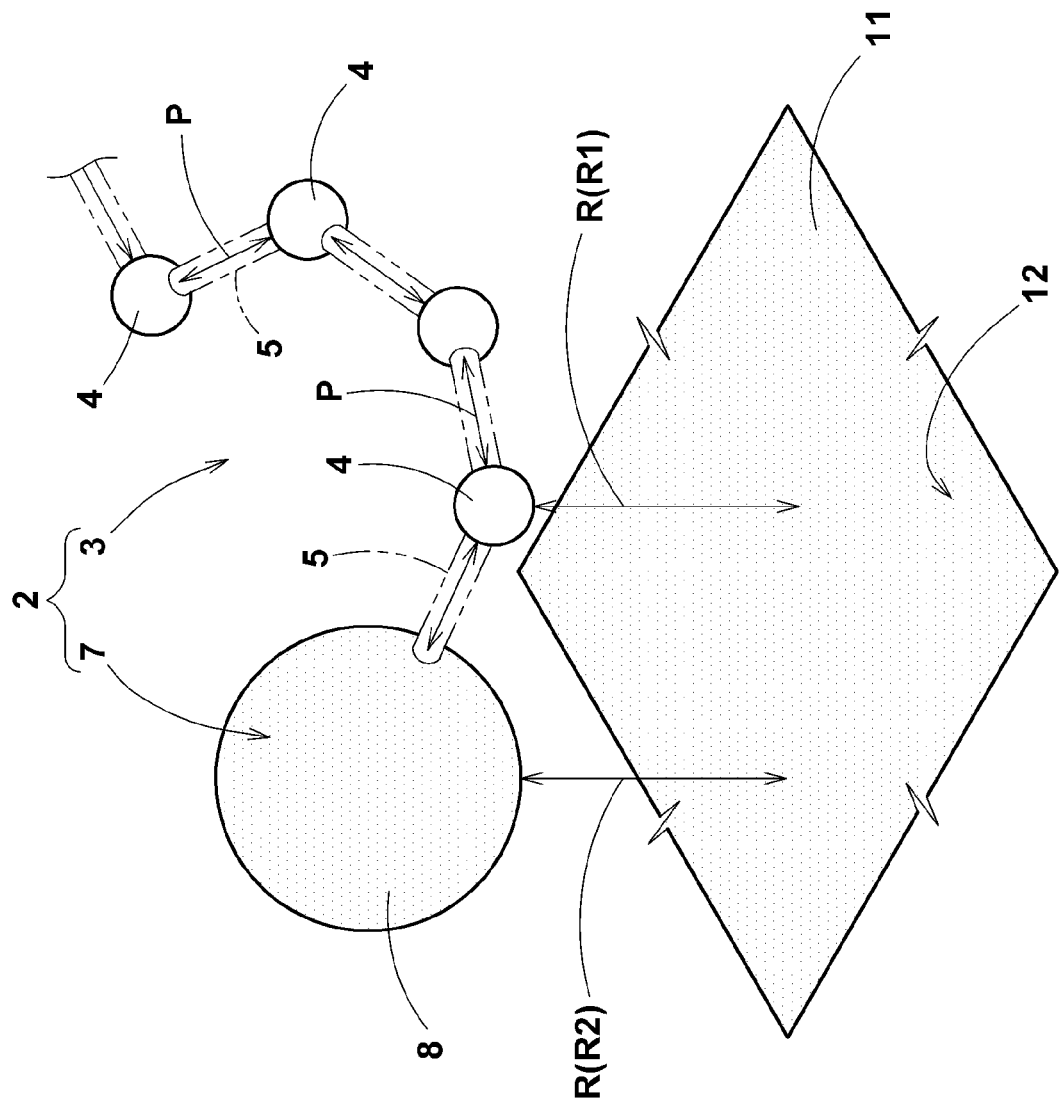
FIG. 7 is a diagram for explaining the potentials defined between the filler model and the modified polymer model.

In the example shown in FIG. 7, the following potentials R1 and R2 are defined.
R1: between filler model 12 and particle 4 (non-modified)
R2: between filler model 12 and particle 8 (modified)

Any suitable values may be set to $\sigma_{wall}$, $\sigma_{wall}$, $\varepsilon_{wall}$ and $r_c$ of the potentials R1 and R2. In this embodiment, these parameters are set as follows.
Potential R1:
$\rho_{wall}=1.0$, $\sigma_{wall}=1.0$
$\varepsilon_{wall}=1.0$, $r_c=1.12$ Potential R2:
σ$_{wall}$=1.0
σ$_{wall}$=1.0,
ε$_{wall}$=5.0 r$_c$=2.5

By setting the value of ε$_{wall}$ of the potential R2 larger than the value of ε$_{wall}$ of the potential R1 as above, the attractive force between the filler model 12 and the particle 8 can increase more than the attractive force between the filler model 12 and the particle 4.

Further, by setting the value of r$_c$ of the potential R2 larger than the value of r$_c$ of the potential R1 and also larger than the value of $2^{1/6}\sigma_{wall}$ as above, the particle 8 (modified) can exert its attractive force on the filler model 12 from a farther distance when compared with the particle 4 (non-modified). Therefore, the affinity to the filler model 12, of the particle 8 is increased in comparison with the particle 4.

On the other hand, the value of r$_c$ of the potential R1 (particle 4/non-modified) is set to be less than $2^{1/6}\sigma_{wall}$ (exert no attractive force) in order to exert only a repulsive force between the particle 4 and the filler model 12.

Simulation process S7

In the simulation process S7, a relaxation of the particles 4 and 8 of the modified polymer models 2 existing between the filler models 12 is simulated by performing molecular dynamics calculations under the above described conditions.

In this example, on the assumption that the particles 4 and 8 of the modified polymer models 2 accords with classical dynamics, Newton's equation of motion is applied to the molecular dynamics calculation. And the motion of the particles 4 and 8 are tracked at constant time interval. During the calculation, the number of the particles in the virtual space 6, and the temperature and the volume of the virtual space 6 are kept constant.

Since the filler model 12 is locked to a pair of the parallelly-opposed wall surfaces 11 of the virtual space 6, the relaxation calculation can be performed, targeting at the modified polymer model 2 only. Therefore, the computational time is remarkable reduced when compared with a relaxation calculation performed targeting at both of the modified polymer models and movable filler models. Further, the direction of the potential field caused by the filler model 12 is one direction perpendicular to the wall surface 11, in contrast to a spherical filler model resulting in radial directions or all directions. Therefore, the relaxation calculation becomes relatively simple and the computational time may be further reduced.

Figure 10:
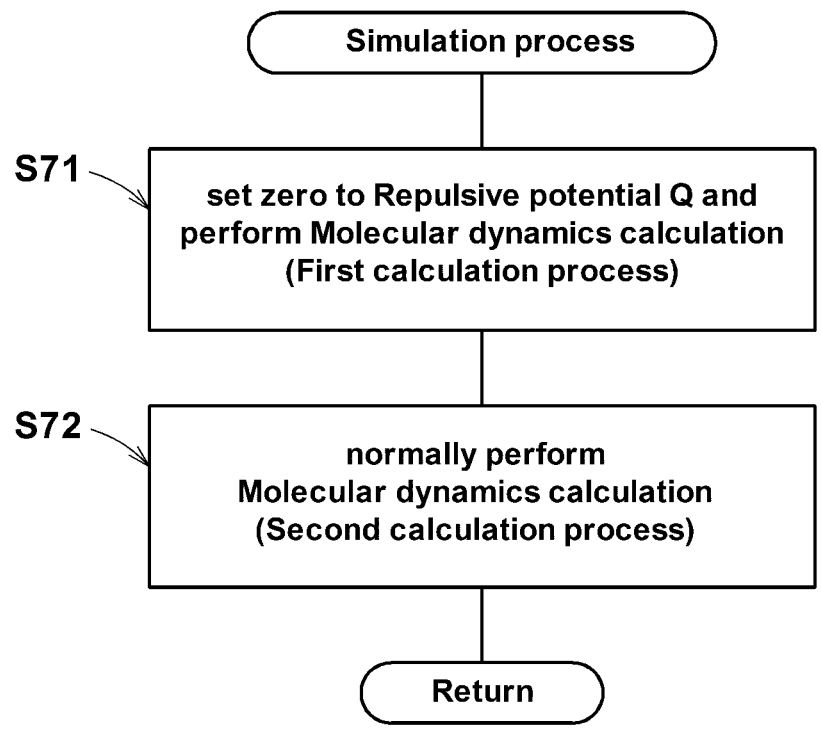
FIG. 10 is a flow chart of the simulation process.

FIG. 10 shows a flowchart of a more specific example of the simulation process S7.

As shown, this example includes a first calculation process S71 and a second calculation process S72 performed thereafter.

In the first calculation process S71, with respect to every possible combinations of the particles 4 and 8 of the modified polymer models 2, the repulsive potential Q (FIG. 5) is defined such that the resultant repulsive force is always zero, and under such condition, a molecular dynamics calculation is performed.

In the second calculation process S72, a molecular dynamics calculation is normally performed without mandatorily setting zero to the repulsive force resulted from the repulsive potential Q.

In the first calculation process S71, therefore, by mandatorily setting zero to the repulsive force, it becomes possible, in the calculation, that the modified polymer models 2 in the virtual space 6 are moved without hindering each other. Therefore, it is possible that each modified polymer model 2 comes close to another modified polymer model 2.

For example, by setting zero to the coefficient E of the equation (2) adjusting the intensity of the repulsive potential Q, the repulsive force is made zero.

The number of steps to make the molecular dynamics calculation in the first calculation process S71 is not less than 100 to sufficiently disperse the modified polymer models 2 but not more than 10,000,000 to avoid unnecessary computational time and cost.

In the second calculation process S72, similarly, the number of steps to make the molecular dynamics calculation is not less than 100 and not more than 10,000,000.

Thus, through the first calculation process S71, the modified polymer models 2 are well dispersed in a short period of time.

Then, through the second calculation process S72, the molecular dynamics calculation is performed under the normal conditions. Therefore, it is possible to make an accurate relaxation in a short period of time.

Process S8

In the process S8, using the data obtained through the simulation process S7, the filler models 12 and modified polymer models 2 are rendered for example as a three-dimensional view and output by the use of a display, printer or the like.

Process S9

In the process S9, which is implemented by humans differently from the above processes, the affinity of the modified polymer model 2 to the filler model 12 is evaluated based on how much the particle 8 (modified) approaches the filler models 12.

Figure 9:
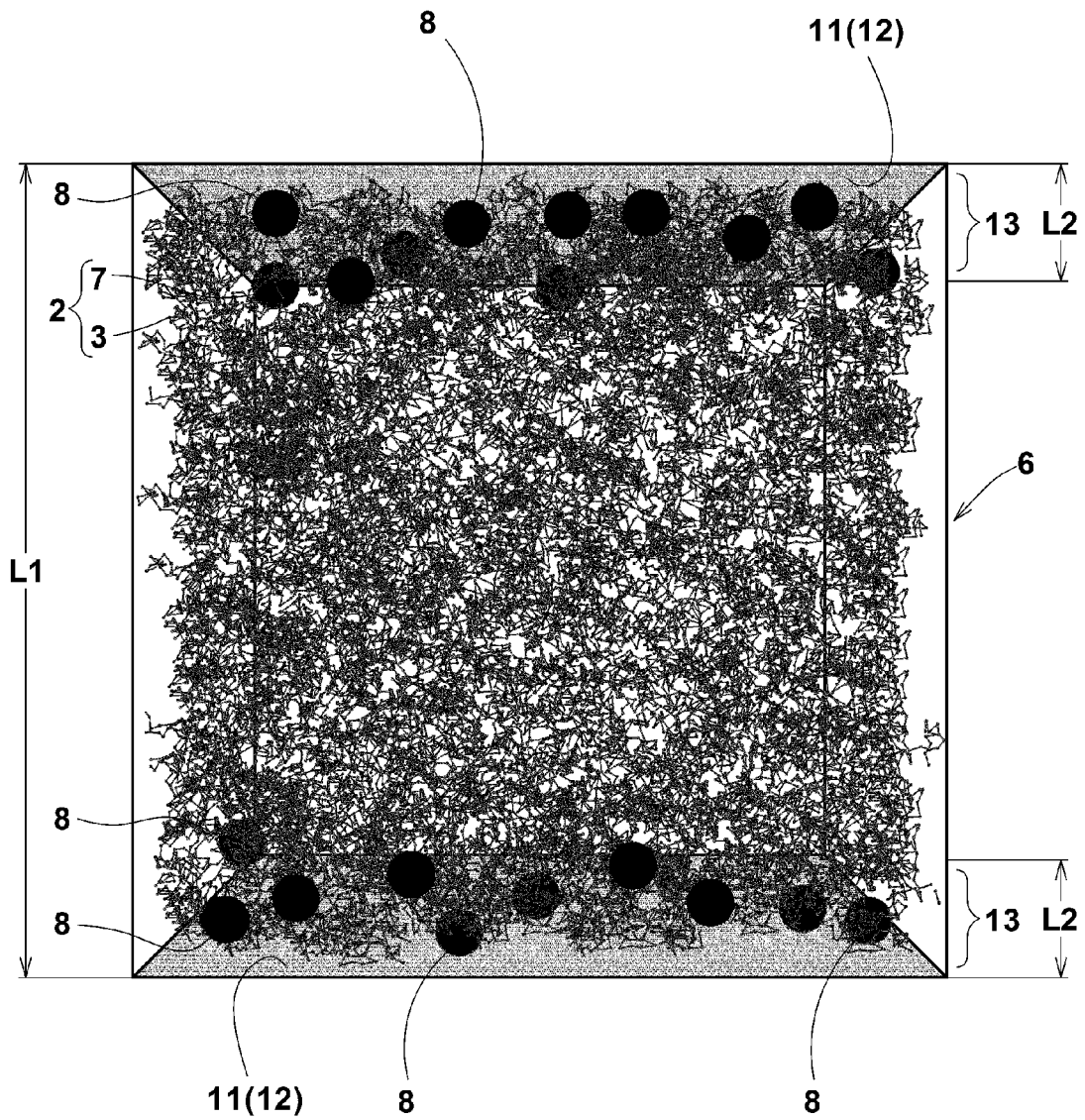
FIG. 9 shows a state of the modified polymer models in the virtual space after the relaxation calculation has been completed according to an embodiment of the present invention.

According to the present invention, the filler models 12 are the flat surfaces at the fixed positions, therefore, as shown in FIG. 9, it may be intuitively understandable how much the particle 8 approaches the filler models 12.

It is also possible to implement this process S9 by the use of the computer 1. For example, for each of the particles 8 existing between the paired parallelly-opposed wall surfaces 11 namely paired filler models 12, the computer judges whether the distance L2 of the particle 8 from the adjacent filler model 12 is within a predetermined range (for example, 0.05 to 0.15 times the distance D1 between the wall surfaces 11). Then, if within the predetermined range, the computer 1 judges the affinity as being very good.

In any case, if the affinity is judged as being good in the process S9, the simulation is ended.

If the affinity is judged as being not satisfactory, the simulation is again carried out by changing the conditions of the modified polymer model 2 and/or filler model 12.

Comparison Tests

Embodiment 1

Figure 11A:
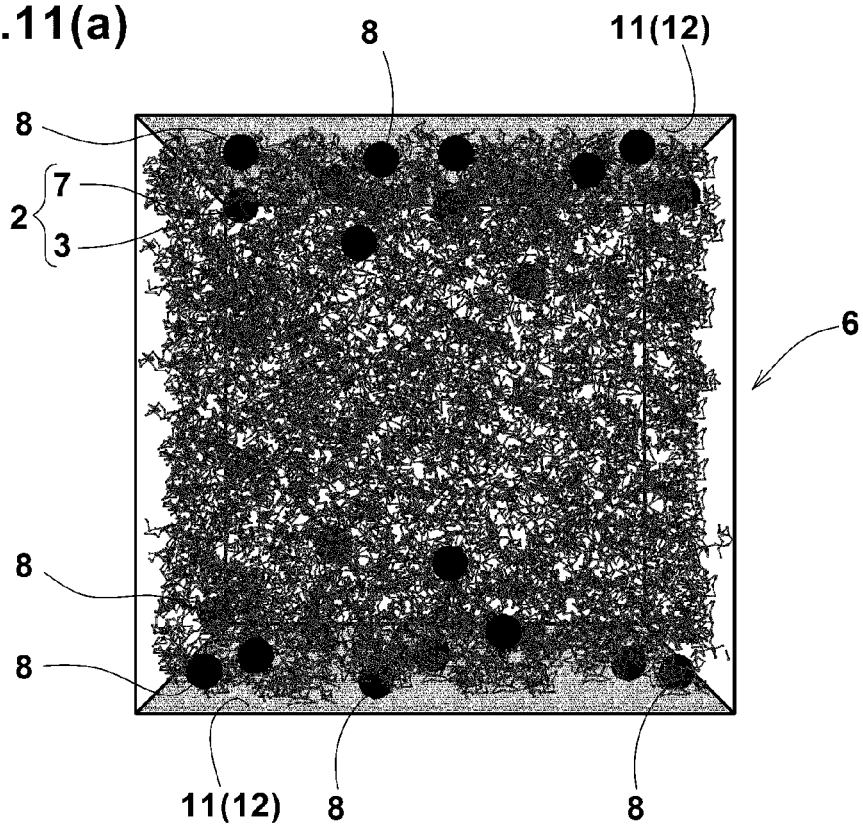
FIG. 11(a) shows a state of the modified polymer models in the virtual space after the first calculation process (1,000,000 steps) has been completed, starting from the initial state show in FIG. 8.

According to the above described method shown in FIGS. 2-3 and 10, starting from the initial state shown in FIG. 8, a state shown in FIG. 11(a), wherein the modified polymer models 2 were well dispersed, could be obtained through the first calculation process S71, then
a state shown in FIG. 9 could be obtained through the second calculation process S72. The number of steps of the first calculation process was 1,000,000. The number of steps of the second calculation process was 50,000. The total computational time from FIG. 8 to FIG. 9 was 24 hours.

Embodiment 2

According to a method in which the first calculation process S71 was omitted, starting from the initial state shown in FIG.

Figure 11B:
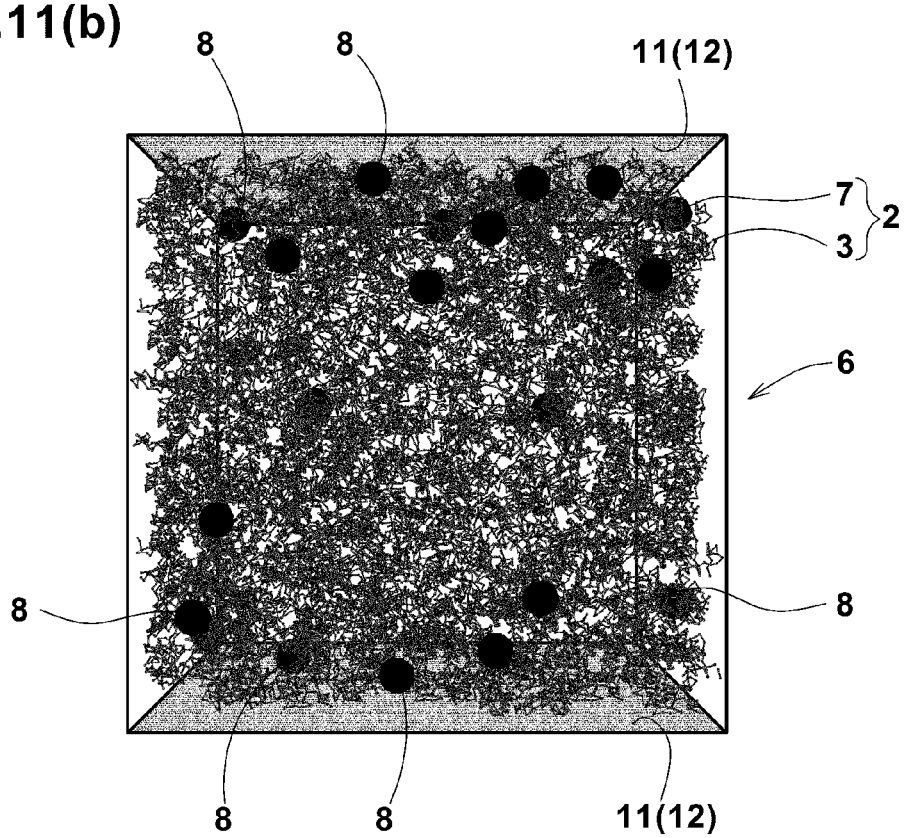
FIG. 11(b) shows a state of the modified polymer models in the virtual space after the second calculation process (1,000,000 steps) has been completed, starting from the initial state show in FIG. 8, without performing the first calculation process.

8, a state shown in FIG. 11(b) wherein the modified polymer models 2 were dispersed middling could be obtained through the second calculation process S71. The number of steps of the second calculation process was 1,000,000. The total computational time from FIG. 8 to FIG. 11(b) was 240 hours.

In the embodiment 1 and embodiment 2, the number of the modified polymer models in the virtual space was 30. The number of the particles in each polymer model was 1,000.

The number of the particles each representing the modifying group was one per a modified polymer model.

The coupling potential P, repulsive potential Q and potential R were defined as explaining in the description above.

Comparative Example

Figure 12:
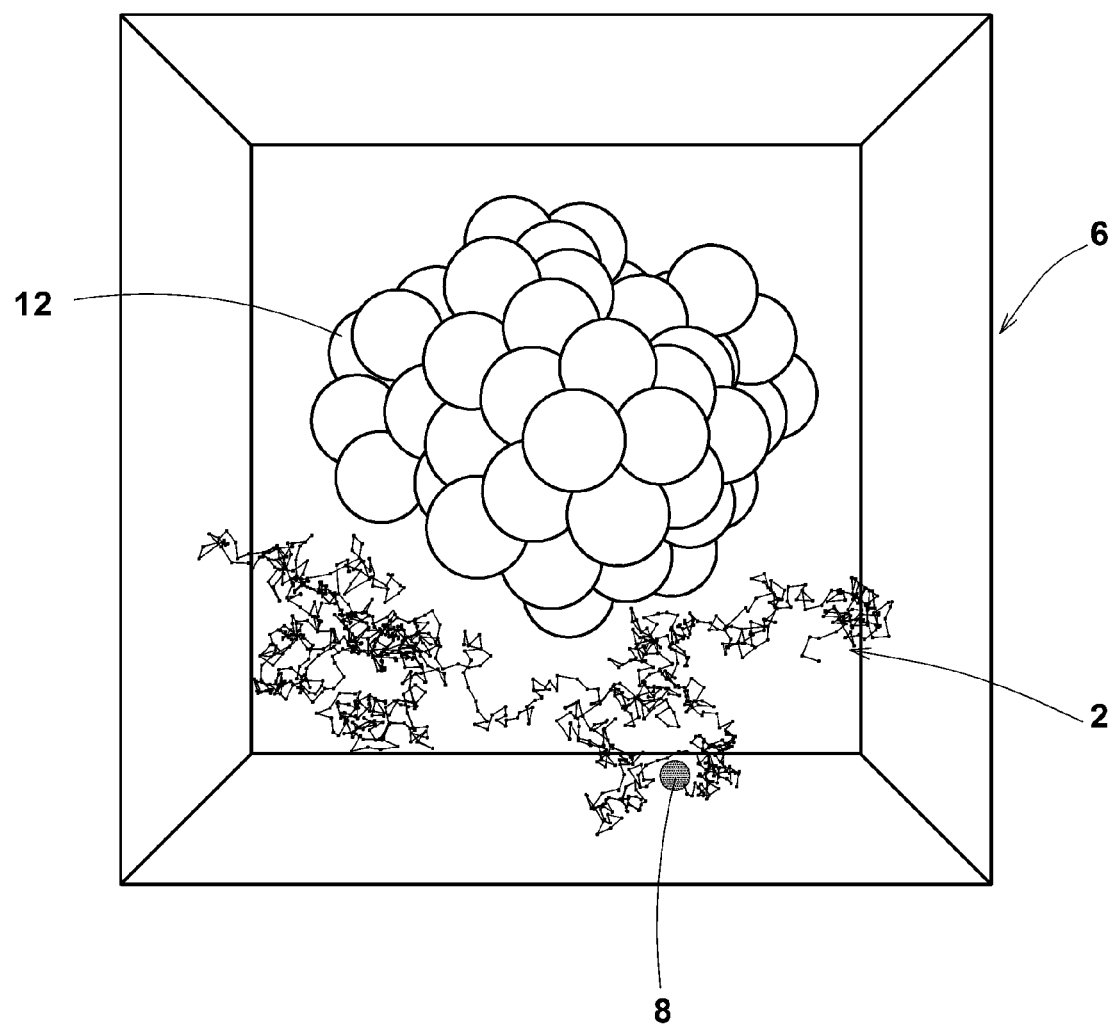
FIG. 12 is shows a combination of the modified polymer models and spherical filler particle models used as a comparative example.

In the case of a method in which, as shown in FIG. 12, filler models 12 each representing a filler particle and the modified polymer models 2 were disposed in the virtual space 6 and their relaxation was computed by a molecular dynamics calculation, 100,000,000 steps and a computational time of 2400 hours were needed in order to complete the relaxation calculation. The number of the filler models was 100. The number of the modified polymer models in the virtual space was 30. The number of the particles in each polymer model was 1,000. The number of the particles each representing the modifying group was one per a modified polymer model.

Although the invention has been described in accordance with the flowchart shown in FIG. 2 with a certain degree of particularity, this flowchart is just for purposes of illustration or for convenience sake and not to be construed to limit the scope of the invention. It is understood by those skilled in the art that the most important point is to define the modified polymer models 2, filler models 12, potentials P, Q and R and various conditions before starting the simulation process S7, therefore, the order from S1 to S6 is not essential. It is to be understood that some of these processes S1-S6 may be performed simultaneously by the computer, and some of these processes S1-S6 may be performed in reverse order.

The invention claimed is:

1. A computer-implemented method for simulating a polymer material comprising a polymer, a filler, and a modifying agent for increasing the affinity of the polymer to the filler, comprising:
    defining a virtual space having a pair of parallelly-opposed wall surfaces;
    defining a pair of filler models by a pair of the parallelly-opposed wall surfaces;
    defining a plurality of modified polymer models disposed in the virtual space,
    wherein each of the modified polymer models includes
    a polymer model of the polymer, comprising at least one particle, and
    a modifying agent model of the modifying agent, comprising at least one particle representing a modifying group of the modifying agent;
    defining a first repulsive potential between the particles of the polymer models such that the first repulsive potential exerts a repulsive force between the particles when the distance therebetween becomes less than a first threshold;
    defining a second repulsive potential between the particles of the modifying agent models such that the second repulsive potential exerts a repulsive force between the particles when the distance therebetween becomes less than a second threshold;
    defining a third repulsive potential between the particles of the polymer models and the particles of the modifying agent models such that the third repulsive potential exerts a repulsive force between the particles when the distance therebetween becomes less than a third threshold;
    defining a fourth potential between the filler models and the particles of the polymer models such that the fourth potential exerts an attractive force between the filler model and the particle when the distance therebetween becomes less than a fourth threshold;
    defining a fifth potential between the filler models and the particles of the modifying agent models such that the fifth potential exerts an attractive force between the filler model and the particle when the distance therebetween becomes less than a fifth threshold larger than the fourth threshold;
    wherein an intensity of the fifth potential is larger than an intensity of the fourth potential;
    performing a relaxation of the modified polymer models disposed in the virtual space though a first calculation process and a second calculation process, wherein
    the first calculation process is such that a molecular dynamics calculation is performed to relax the modified polymer models, mandatorily setting zero to the repulsive forces resulted from the first repulsive potential and the second repulsive potential defined on the particles of the modified polymer models, and
    the second calculation process is such that, with respect to the modified polymer models relaxed through the first calculation process, a molecular dynamics calculation is performed normally without mandatorily setting zero to the repulsive forces resulted from the first repulsive potential and the second repulsive potential defined on the particles of the modified polymer models;
    judging if the affinity of the modified polymer models to the filler models is good, by using the modified polymer models relaxed through the second calculation process, based on the number of the modified particles of which distances from the adjacent filler models are within a predetermined range;
    if the affinity is not good, again carrying out the process of performing a relaxation of the modified polymer models by changing the conditions of the modified polymer models and/or filler models; and
    if the affinity is good, outputting the relaxation state of the modified polymer models in order to develop the polymer material.

2. The method for simulating polymer material according to claim 1, wherein, in at least one of the modified polymer models, the polymer model comprises a plurality of the particles, and a coupling potential as a joining chain is defined between the particles of the polymer model and the modifying agent model,
    wherein the coupling potential dominantly exerts an attractive force whose magnitude is larger than the magnitude of the repulsive force resulting from the first/third repulsive potential defined between the particles when the distance therebetween becomes increased over a distance which is determined by the intensity of the first/third repulsive potential and the intensity of the coupling potential.

* * * * *